United States Patent [19]

Loiterman et al.

[11] Patent Number: 5,041,098

[45] Date of Patent: Aug. 20, 1991

[54] VASCULAR ACCESS SYSTEM FOR EXTRACORPOREAL TREATMENT OF BLOOD

[75] Inventors: David A. Loiterman, Oak Brook, Ill.; Paul V. Fenton, Jr., Marblehead; Thomas M. Young, North Andover, both of Mass.

[73] Assignee: Strato Medical Corporation, Beverly, Mass.

[21] Appl. No.: 354,614

[22] Filed: May 19, 1989

[51] Int. Cl.$^5$ .............................................. A61M 5/00
[52] U.S. Cl. .................................... 604/175; 604/93
[58] Field of Search .......................... 604/4, 8–10, 604/85, 86, 93, 131, 132, 140, 174, 175, 185, 244, 283, 891.1, 905

[56] References Cited

U.S. PATENT DOCUMENTS

| | | |
|---|---|---|
| 3,310,051 | 3/1967 | Schulte . |
| 3,490,438 | 1/1970 | Lavender et al. .................. 604/4 |
| 4,014,328 | 3/1977 | Cluff et al. . |
| 4,108,174 | 8/1978 | Slivenko . |
| 4,368,730 | 1/1983 | Sharrock ......................... 604/158 |
| 4,464,178 | 8/1984 | Dalton ............................ 604/174 |
| 4,490,137 | 12/1984 | Moukheibir ..................... 604/28 |
| 4,569,675 | 2/1986 | Prosl et al. ...................... 604/175 |
| 4,581,020 | 4/1986 | Mittleman ....................... 604/175 |
| 4,673,394 | 6/1987 | Fenton, Jr. ...................... 604/175 |
| 4,687,468 | 8/1987 | Gianturco ....................... 604/153 |
| 4,692,146 | 9/1987 | Hilger ............................. 604/93 |
| 4,704,103 | 11/1987 | Stöber et al. .................... 604/175 |
| 4,710,167 | 12/1987 | Lazorthes ....................... 604/93 |
| 4,772,270 | 9/1988 | Wiita et al. ...................... 604/175 |
| 4,778,452 | 10/1988 | Moden et al. ................... 604/93 |
| 4,781,680 | 11/1988 | Redmond et al. ............... 604/891.1 |
| 4,861,341 | 8/1989 | Woodburn ...................... 604/175 |
| 4,886,501 | 12/1989 | Johnston et al. ................ 604/175 |
| 4,892,518 | 1/1990 | Cupp et al. ...................... 604/175 |

FOREIGN PATENT DOCUMENTS 0134745 3/1985 European Pat. Off. .
2612784 9/1988 France ............................ 604/891.1

OTHER PUBLICATIONS

Colton et al. (1981) *The Kidney* (2nd Ed.) Brenner and Rector, Jr., eds., W. B. Saunders Co., Phila., vol. II, pp. 2425–2489.

Mahurkar (1985) *Trans. Am. Soc. Artif. Intern. Organs* *XXXI*:124–130.

Strato Medical Corporation (1985) LifePort Vascular Access System booklet.

*Primary Examiner*—Stephen C. Pellegrino
*Assistant Examiner*—Ralph A. Lewis
*Attorney, Agent, or Firm*—Lahive & Cockfield

[57] ABSTRACT

Disclosed are implantable, vascular access ports and vascular access systems including such ports. These ports include a biocompatible housing having at least one internal open-faced chamber extending along a reference axis, and defined by a concave sidewall and a bottom wall. The concave sidewall is concave in the direction of the axis and forms a lateral sidewall for the chamber. The port further includes a septum of biocompatible, self-resealing, penetrable material affixed to the housing and spanning the periphery of the open face of the chamber. A cannula is attached at a first end to the housing and extends laterally from that end. Its second end is adapted to receive a catheter. The cannula further includes internal walls defining a channel extending from the first end, along a channel axis from a point on the lateral boundary of, and in communication with, the chamber to the second end.

17 Claims, 6 Drawing Sheets

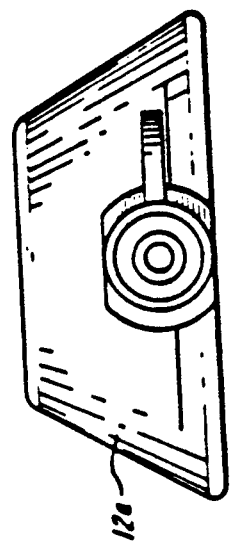
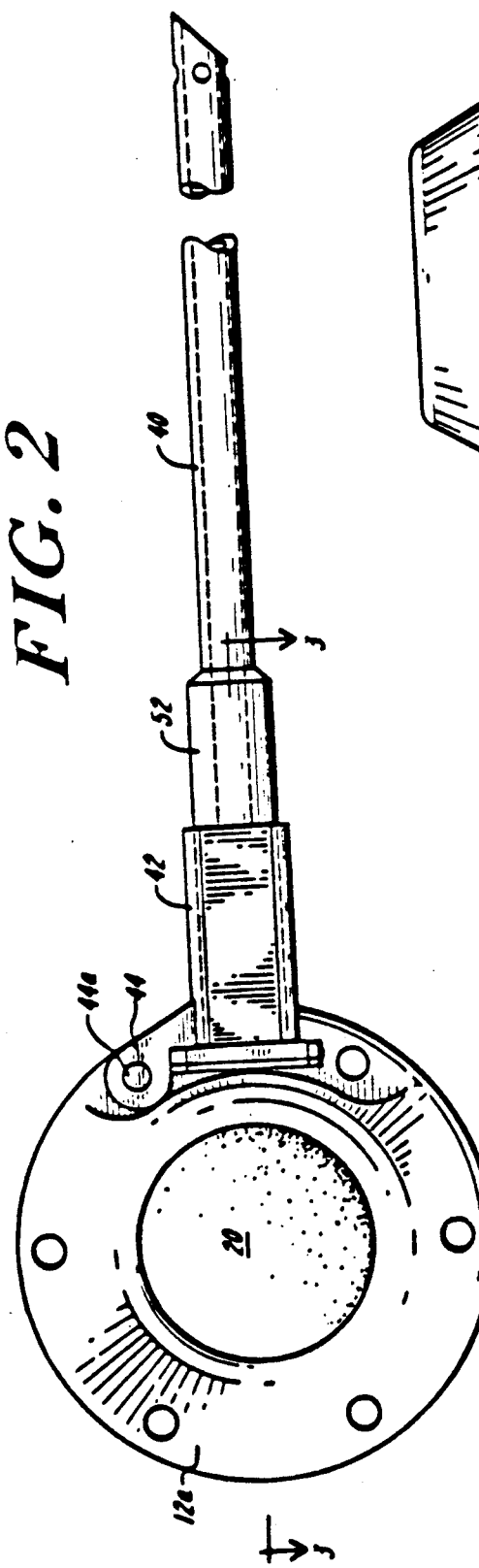
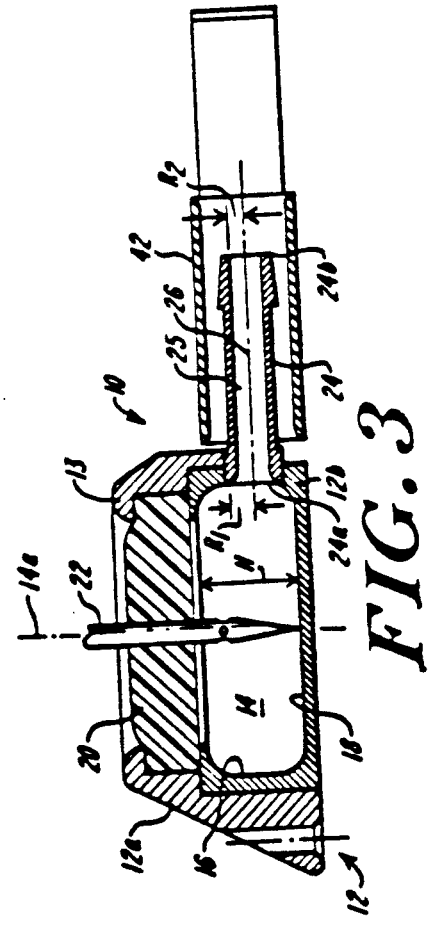

VASCULAR ACCESS SYSTEM FOR EXTRACORPOREAL TREATMENT OF BLOOD

BACKGROUND OF THE DISCLOSURE

This invention relates to the treatment of blood, and more particularly to systems and implantable devices providing direct access to the vascular system of a patient receiving extracorporeal blood treatment.

The extracorporeal treatment of blood requires that the vascular system of a subject be directly accessed, and often accessed repeatedly. Such treatments include the removal of various components or toxins, and the addition of oxygen to the blood.

For example, hemapheresis is a treatment which involves the collection of blood cells, the removal of a specific blood cell type from the blood, or plasma exchange. It requires that the vascular system be tapped with, for example, a needle attached to a catheter. The blood is then circulated through an extracorporeal separating device, and then returned to the vascular system via a second needle stick. Hemapheresis may be performed once or repeatedly providing that adequate time is allowed for replacement of the blood cell by the donor's bone marrow.

Another blood treatment is hemodialysis, or the removal of various chemical substances from the blood. Such substances include ingested or injected drugs, or toxins created during normal body metabolism, the presence of which is most often due to renal impairment. Typically this treatment involves accessing the vascular system, connecting the vasculature to a hemodialysis pump and filtration mechanism, and returning the cleansed blood to the vascular system.

Accessing the vascular system may be achieved by temporary or permanent means, depending on the requirements of the patient. For example, methods are available to establish temporary access involving the percutaneous insertion of a single or double lumen cannula into a large vein such as the subclavian, femoral, or internal jugular.

However, to provide more adequately for the chronic renal impaired patient, it is preferable to surgically rearrange the peripheral vasculature, thereby creating a permanent access. The procedure usually involves connecting a large surface peripheral vein to an artery producing a fistula, or surgically creating a loop between an artery and a vein using a synthetic material such as expanded PTFE. The natural fistula, normally constructed from a vein or venous graft, is preferred over the synthetic loop which is prone to complications such as infections, clotting, and leakage. In either case, the surgery involved in its creation is a lengthy process, and maintaining the resulting reconstruction of the vasculature is a chronic problem. The fistula must mature or become arterialized before it can be accessed with the needles. Then, when it becomes functional, a number of complications may arise including clotting, thrombosis, infection, and infiltration of scar-forming cells. In addition, because hemodialysis is a chronic treatment, the required and repeated needle punctures eventually weaken and destroy the arterialized vein, which, to begin with, is abnormally pressurized and particularly susceptible to collapse.

Cleansing of the blood alternatively may be conducted by peritoneal dialysis, a treatment which does not necessitate accessing the vascular system. Peritoneal dialysis involves placing a dialysate solution into the peritoneal cavity of a patient via a catheter. The catheter is surgically implanted such that one end is secured within the cavity and the other end is accessible by either projecting through the skin or can be accessed subcutaneously (see for example, U.S. Pat. No. 4,490,137). The dialysate is allowed to remain in the cavity for a predetermined time to allow blood metabolites or toxins (solutes) to cross the highly vascularized peritoneal membrane and enter into the dialysate. The toxin-laden dialysate is later removed through the same catheter.

However, peritoneal dialysis may not be as desirable as hemodialysis because it rids the blood of metabolities indirectly using the peritoneal membrane as a filter and in fact, only 15% of patients currently receiving blood dialysis therapy undergo peritoneal dialysis.

Implantable and extracorporeal devices are known for the infusion of medicines and drugs into the vasculature (see, e.g., U.S. Pat. Nos. 4,673,394, 4,704,103, 4,692,146, and 4,014,328). However, such devices are not useful for extracorporeal blood treatments, as their construction does not take into account the fragile nature of blood elements which are highly susceptible to breakage, or hemolysis during transfer, intrinsic clotting, and immune response.

The implantable vascular access port disclosed in U.S. Pat. No. 4,673,394 includes a housing portion having a substantially right circular cylinder shaped, open-faced internal chamber, and a septum spanning the open face of the chamber to establish a closed reservoir. A cylindrical, tubular cannula extends from the sidewall of the chamber for coupling the reservoir to an external catheter. With such a configuration, the chamber and cannula geometries are ill-suited for the transfer of blood elements through the access port, particularly at the flow rates and pressures that are required for current hemodialysis techniques. As blood is transferred through the septum and injected into the chamber, flow patterns are established which include "dead flow" pockets, particularly in the corners of the chamber. Blood cells which enter these pockets merely circulate therein or hardly move at all, and never, or only after a long time, enter the flow through the cannula. Such movement or lack thereof increases the chances of coagulation of the blood. Further, at the relatively high flow rates, cell-lysing collisions occur at the abrupt interface of the chamber and the cannula. Such collisions are both from cell-to-cell interactions within regions of turbulence and from the physical impact of cells within the chamber sidewalls.

Therefore, it is an object of the present invention to provide an improved method of accessing the vascular system which is antiseptic, less traumatic to the patient, and which has potential for self-access or home care.

It is another object of the invention to provide an easier, quicker method of providing a vascular access which will not require maturation before it can be used for various extracorporeal blood treatments.

It is also an object to provide an improved vascular access device which can be reliably and repeatedly connected to an extracorporeal blood treatment, and which is durable and easy to use.

SUMMARY OF THE INVENTION

Briefly, the present invention is directed to an implantable vascular access port for use in the extracorporeal treatment of blood or fractions thereof. The port includes a biocompatible housing having an internal open-faced chamber defined by a concave sidewall and a bottom wall. A septum composed of a biocompatible, self-resealing, penetrable material is affixed to the housing and spans the periphery of the open face of the chamber. To the housing is attached the first end of a cannula. The cannula extends laterally from the housing, and has a second end adapted to receive a catheter. In addition, the cannula has internal walls defining a channel extending from its first end, along a channel axis from a point on the lateral boundary of the chamber, to its second end. This channel has a radius R1 at the first end of the cannula, and has a radius R2 at the second end of the cannula, R1 being greater than R2. Preferably, the decrease in radius of the channel frame R1 to R2 is monotoxic, and provides a smooth and continuously bounded flow path.

The housing of the access port may have lock means formed adjacent to the port for releasably engaging a flange of a mating twist-lockable connection. The lock means includes a region of the bounding surface of the housing defining a void region adjacent to the port exterior to the chamber. The lock means also includes means for releasably engaging the flange by a partial revolution of such connection, whereby the chamber may be placed in fluid communication with a catheter having such a mating twist-lockable connection.

In addition, the lock means may include a means for guiding the catheter connector for rotational motion about an axis passing through the port, and further, a means for capturing the connector so as to prevent its movement along that axis when rotated.

In various embodiments of the invention, the housing of the port includes first and second body members. The first member includes a sidewall and a bottom wall having a cylindrical outer side surface. The second body member is annular (including a cylindrical inner side surface), and includes means for supporting the septum. The outer surface of the first member is adapted to interfit with the inner side surface of the second member. The housing may further include two or more internal open face chambers, each of which having an affixed septum and an attached cannula.

In another form of the invention, an implantable vascular access system is provided whereby the vascular access port is coupled to a catheter having a central passage with radius R2 and an entry port defining a flow path to the central passage along a central axis. The coupling means detachably couples the cannula and the entry port, while selectively establishing a continuous flow path between the chamber and the central passageway, the channel axis and the central axis being coaxial.

The vascular access system may employ a catheter with a wirewound reinforcing sidewall, and with an end opposite the entry port that is beveled and/or has at least one lateral aperture adjacent thereto. The system may further include a non-coring needle adapted to selectively penetrate the septum.

BRIEF DESCRIPTION OF THE DRAWINGS

The foregoing and other objects of this invention, the various features thereof, as well as the invention, itself, may be more fully understood from the following description, when read together with the accompanying drawings in which:

FIG. 2 shows a top plan view of the access port of FIG. 1;

FIG. 3 shows a sectional view along lines 3—3 of the access port of FIG. 2;

FIG. 4 shows a side elevation view of the access port of FIG. 2 as viewed from the axis of the cannula;

DESCRIPTION OF THE PREFERRED EMBODIMENT

Extracorporeal blood treatments such as hemodialysis, plasmapheresis, and hemofiltration require high flow rates to assure adequate clearances, but at pressures low enough to avoid hemolysis and obligatory ultrafiltration. Optimization of blood flow and pressure resistance through the access port is therefore a critical factor in constructing a functional vascular access system. Other considerations include the preservation of blood vessels and blood constituents, and the minimization of access trauma and patient discomfort.

The vascular access system of the present invention has been designed with the above-mentioned criteria in mind. This system enables blood to be removed from, and returned back to the vascular system of the body with minimum trauma to accessed blood vessels and blood elements. It can be heparinized to reduce the chance of coagulation therein, and closed off when not in use. In addition, the port reservoir, the catheter, the coupling, and the transitions therethrough have been designed to reduce areas of reduced movement or dead space, thereby minimizing the chance that coagulation may occur.

Figure 1:
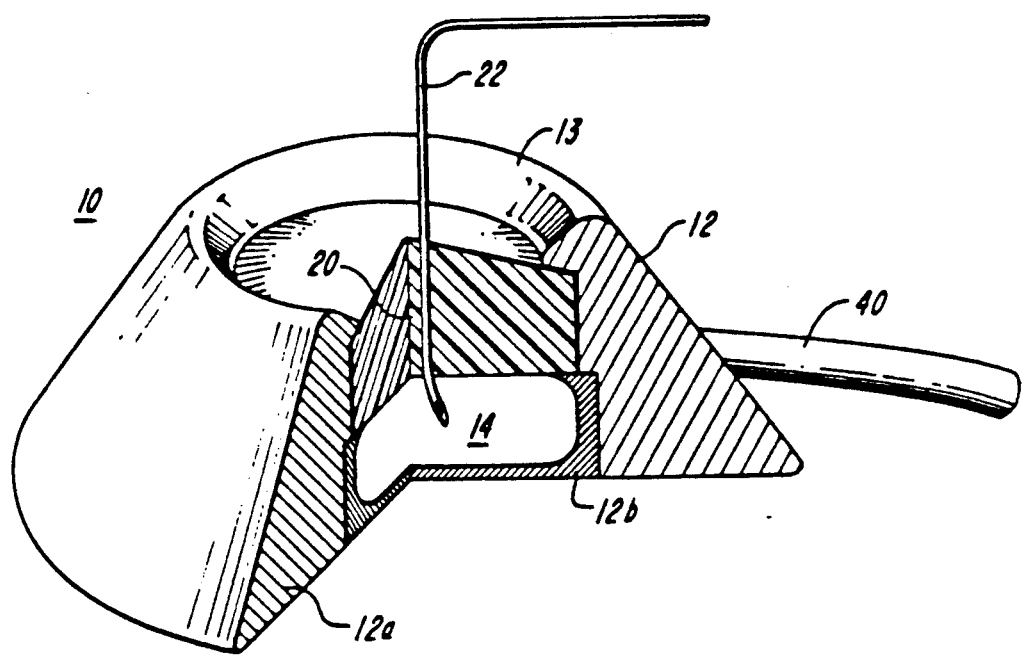
FIG. 1 shows a cutaway view of an implantable access port according to the invention.

FIG. 1 shows a cutaway pictorial view of an implantable access port 10 according to the present invention FIGS. 2, 3 and 4 show top plan, sectional and end elevation views, respectively, of the access port 10 of FIG. 1. Access port 10 includes a two component housing 12 defining a generally cup-shaped internal open-faced chamber 14 defined by sidewalls 16 and bottom wall 18. The open face of chamber 14 is closed off by a cover member (or septum) 20 which spans the periphery, or lip, of the chamber 14.

Septum 20 is formed of a biocompatible, self-resealing penetrable material, which is preferably an elastomer, such as silicone rubber or latex. Septum 20 is adapted to permit access using a hypodermic needle 22 to the chamber 14.

In the illustrated embodiment, the housing 12 includes an outer body member 12a and an inner body member 12b. In the preferred embodiment, both body members 12a and 12b are formed of a biocompatible material, such as titanium, although surgical grade steel or other biocompatible hard materials can be used. The inner body member 12b includes a generally cylindrical outer lateral surface. The outer body member 12a is generally annular and has a cylindrical inner side surface with a radius substantially matching the outer lateral surface of inner body member 12b, so that the two body members interfit and may be press-fit together to form housing 12. A lip 13 captures the peripheral portion of septum 20. The outer body member 12a has apertures therein, evenly spaced about its perimeter, for suturing the access port to patient tissue when implanting.

The inner body member 12b includes the internal sidewall 16 and the bottom wall 18 which define chamber 14. The internal sidewall 16 is concave in the direction of axis 14a and the bottom wall is generally planar, although there may be some minor variation. An upper lip 15 of inner body member 12b supports the peripheral portion of septum 20.

A cannula 24 is attached at its proximal end to housing 12. Cannula 24 extends laterally from housing 12. The distal end 24b of cannula 24 is adapted for receiving a catheter. The cannula 24 includes internal walls that define a fluid flow channel 25 extending from a point in chamber 14, through the sidewall 16 and along a channel axis 26 to the distal end 24b of cannula 24.

The channel has a radius R1 at the proximal end 24a and a radius R2 at the distal end, where R1 is greater than R2. In the preferred embodiment, R1 is 3.4 mm and R2 is 2.4 mm. The decrease in radius of the channel 25 from R1 to R2 is monotonic and is localized near the proximal end 24a, although a more gradual change may also be used. Preferably, the rate of change of radius of channel 25 and the curvature of the sidewall 16 defining chamber 14 is optimally determined to establish an efficient blood flow path between chamber 14 and the distal end 24b of cannula 24.

Figure 4A:
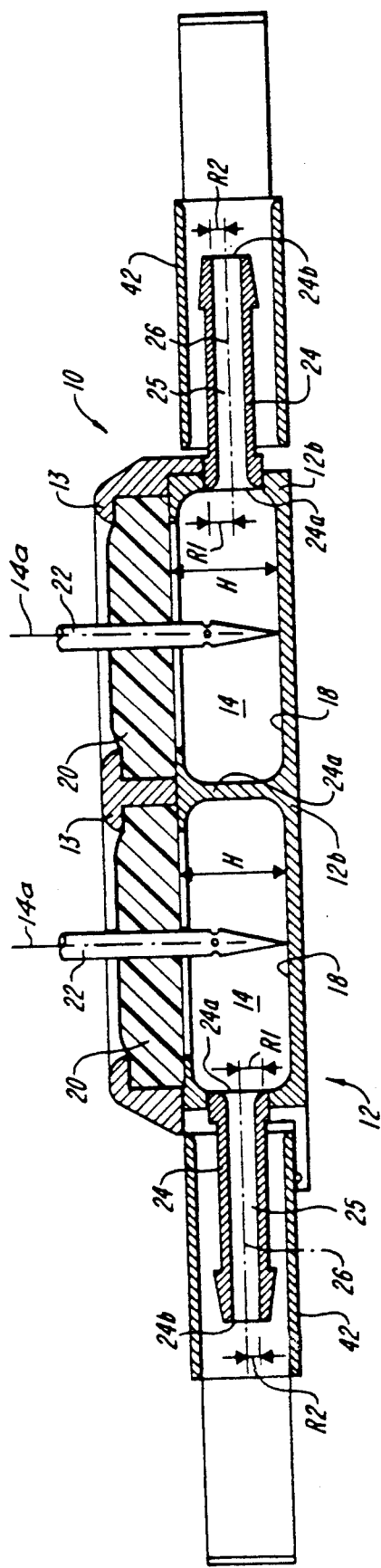
FIG. 4A shows an embodiment of the invention including two chambers similar to the chamber of FIGS. 2-4.

FIG. 4a shows a two-chamber embodiment of the invention, where each chamber is similar to the chamber of the embodiment of FIGS. 2-4.

The needle shown in FIG. 1 is substantially the same as a Huber type non-coring needle. For blood flow applications, the needle is 16 gauge, having an inner bore diameter of 1.19 mm. This relatively large diameter is adapted to permit relatively high flow rates of blood, for example, 300 cc/min.

An alternative form of needle 22 is shown in FIG. 3. This needle, shown in detail in FIGS. 5-7, includes a solid trocar (three plane) point and a pair of opposed lateral ports near the point region 22a. In other embodiments, a single lateral port may be used. The needle 22 is a 16 gauge needle, having an inner bore diameter 1.19 mm, also to accommodate desired blood flow rates. In the preferred embodiment, where the height H of chamber 14 is 8 mm mm and the maximum diameter is 22 mm, the ports of needle 22 have a 1 mm diameter and are 6 mm from the tip.

Figure 5:
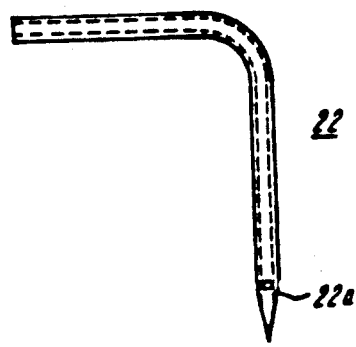
FIG. 5 shows a side elevation of a needle for use with the access port of FIGS. 1-4.
Figure 6:
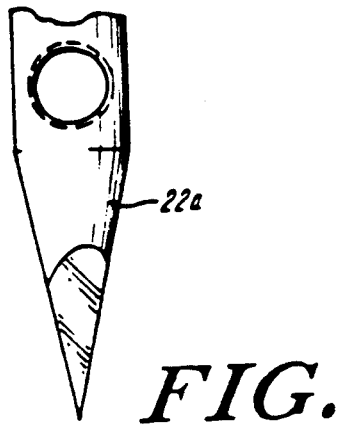
FIG. 6 shows a side elevation view of the tip of the needle of FIG. 5.
Figure 7:
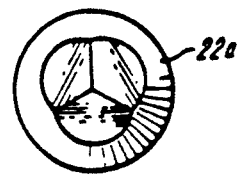
FIG. 7 shows an end view of the tip of the needle of FIG. 5 as viewed from the needle axis.

With the configuration of FIGS. 2-4 and the needle of FIGS. 5-7, the flow pattern for human blood injected into chamber 14 is characterized by substantially improved flow characteristics within chamber 14 which are aimed at reduced flow separation (i.e., eliminating dead flow spaces which could cause clotting), even at flow rates as high as 300 cc/min.

Figure 8:
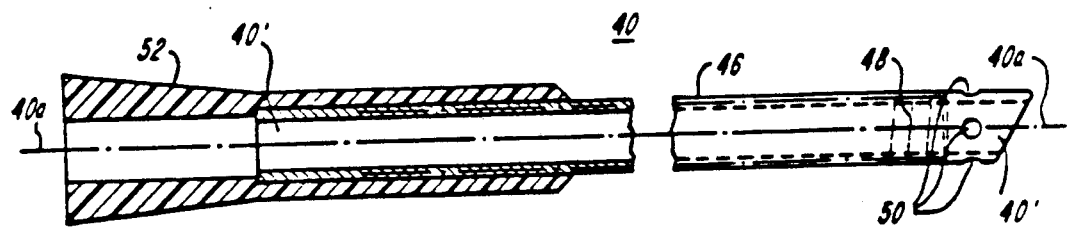
FIG. 8 shows in section a catheter for use with the access port of FIGS. 1-4.

In FIG. 2, an implantable catheter 40 is shown with one end 40' coupled to the cannula 24 within a cylindrical metallic coupler 42 having a laterally extending securing tab 44 with a hole 44a. That catheter 40 is shown in section in FIG. 8. Catheter 40 includes an elongated, flexible tubular section 46 extending along a catheter axis 40a. Catheter 40 is straight cut at the end 40' intended for coupling to access port 10 and is bevel cut at the other end 40''. A plurality of ports 50 are positioned in the sidewalls of catheter 40 near end 40''. In the illustrated embodiment, catheter 40 is particularly adapted for receiving human blood and transferring that blood by way of port 10 for extra-corporeal processing, for example, hemodialysis, as described in conjunction with FIG. 12 below. Since that procedure requires pumping of blood from the patient's body, the catheter section 46 includes a helically wound reinforcement wire 48 within its sidewalls to provide sufficient stiffness to prevent collapse during pumping and binding.

A resilient bushing 52, for example, made of silicone, is positioned over and extends from the coupling end 40' of catheter section 46. The bushing 52 is adapted to position the distal end of cannula 24 (having radius R2) and the coupling end of catheter section 46 (also having radius R2) in a butt joint alignment, so that the inner walls of cannula 24 (defining channel 25) and the inner walls of catheter section 46 at end 40' establish a smooth and substantially continuous flow path defining surface.

In order to secure the catheter 40 to the access port 10, coupler 42 is positioned over the bushing 52, compressing that bushing against the outer surface of cannula 24. Then that coupler 42 is positioned so that the hole 44a securing tab 44 overlies one of the peripheral holes in housing 12. In use, the tab 42 may be sutured to the housing 12 through the overlying holes.

Figure 9A:
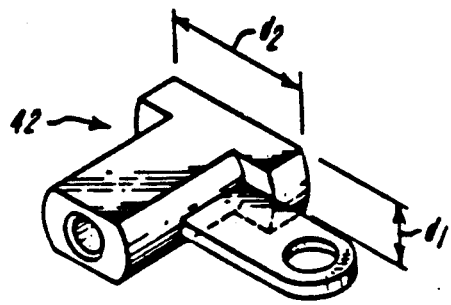
FIGS. 9A and 9B show a coupler for use with the catheter of FIG. 8.
Figure 9B:
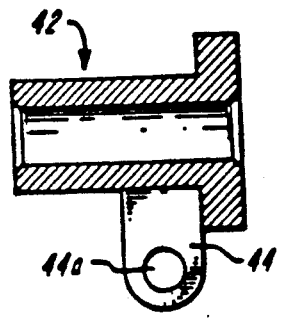
Figure 10:
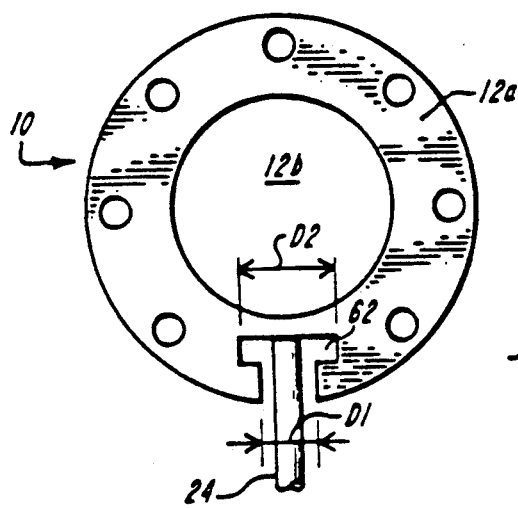
FIG. 10 shows a bottom view of a vascular access port for use with the coupler of FIGS. 9A and 9B.
Figure 11:
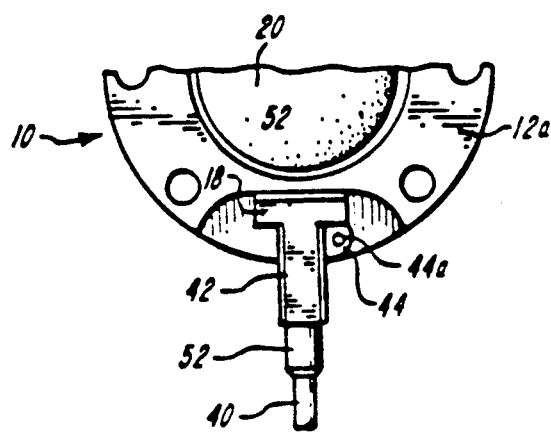
FIG. 11 shows a top plan view of a portion of the access port of FIG. 10 together with a catheter and coupler.

In alternate embodiments, the coupler 42 may have a T-shaped cross-section, as shown in FIGS. 9A and 9B (with or without tab 44) and the housing 12 may be a T-shaped void region 62 surrounding the cannula 24, as shown in FIG. 10. With this configuration, the coupler 42 may be used to effect a twist lockable attachment of catheter 40 to access port 10, as illustrated in FIG. 11. The separable port and catheter assembly, enables the surgeon to be flexible as to where and how the port is implanted.

Figure 13:
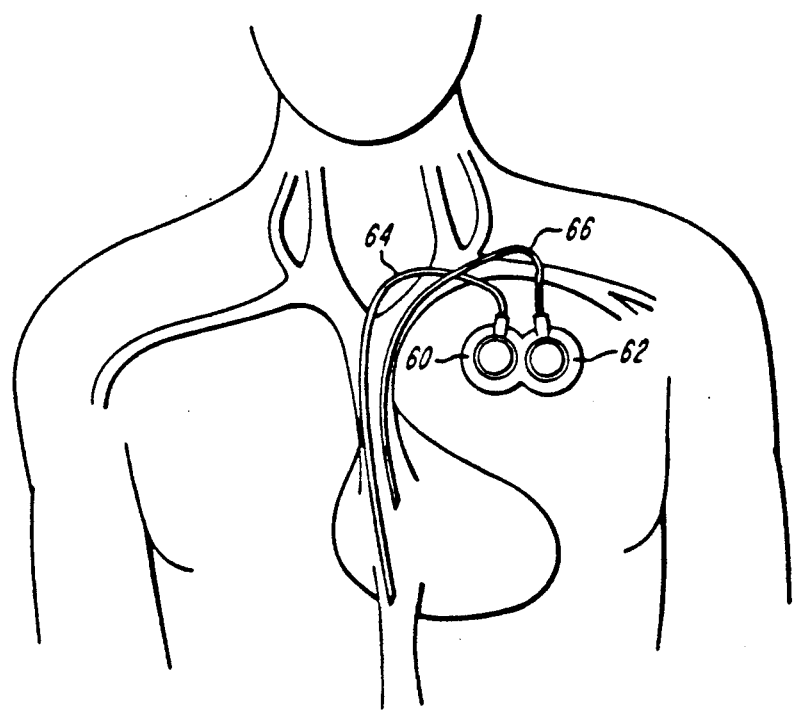
FIG. 13 illustrates the use of an alternative embodiment of the present invention as an access system for extra corporeal blood treatment.

In another embodiment of the invention, the access port has two or more reservoirs in a unitary housing, each having their own individual catheters or catheter lumens attached thereto (FIG. 13).

Figure 12:
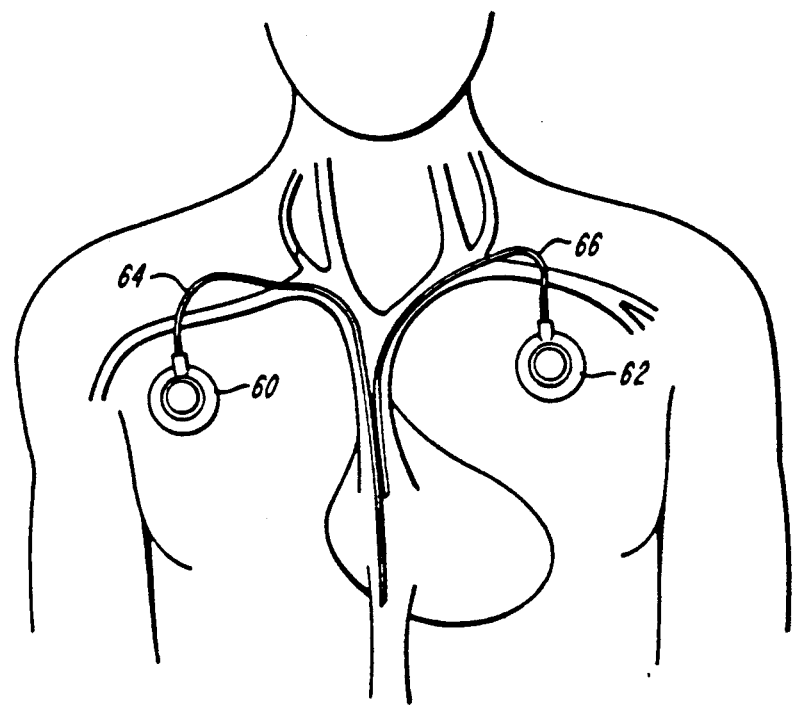
FIG. 12 illustrates the use of one embodiment of the present invention as an access system for extracorporeal blood treatment.

The access system, including the access port, catheter, and coupling means, may be surgically implanted within the body (e.g., in the vasculature of the chest), such that the port is just beneath the epidermis and above the musculature, and the catheter has accessed the vasculature through a major vessel such as the subclavian vein. As shown in FIG. 12, the system preferably includes both an input port 60 and a removal port 62, with catheters 64 and 66 attached thereto and implanted in separate locations in the vasculature (preferably the heart). The ports may accessed transdermally with a needle as described above. Upon termination of extracorporeal treatment, the needle accessing the removal port 62 may be removed, followed by the removal of the input port 60-accessing needle.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

We claim:

1. An implantable vascular access device including a port comprising:
   (a) a biocompatible housing having an internal open-faced chamber extending along a reference axis and defined by a sidewall forming a lateral boundary and being concave in the direction of said axis, and a bottom wall;
   (b) a septum affixed to said housing and spanning the periphery of the open face of said chamber, said septum including a biocompatible, self-resealing, penetrable material; and
   (c) a cannula attached at a first end thereof to said housing and extending laterally therefrom, and having a second end thereof adapted to receive a catheter,
   said cannula further having internal walls defining a channel extending from said first end, along a channel axis from a point on said lateral boundary of, and in communication with, said chamber, to said second end, wherein the transition between said lateral boundary of said chamber and said internal walls of said canula is smooth.

2. An access port according to claim 1, wherein said housing comprises lock means formed adjacent to said port for releasably engaging a flange of a mating twist-lockable connection,
   said lock means including a region of the surface which forms the boundary of said housing,
   said region defining a void region adjacent to said port exterior to said chamber, and including means for releasably engaging said flange by a partial revolution of such connection,
   whereby the chamber may be placed in fluid communication with a catheter having such a mating twist-lockable connection.

3. An access port according to claim 2, wherein said lock means includes a means for guiding said catheter connector for rotational motion about an axis passing through said port, and means for capturing said connector so as to prevent motion of said connector along said axis when rotated.

4. An access port according to claim 1, wherein said housing includes a first body member and a second body member,
   said first body member including said sidewall and said bottom wall having a cylindrical outer side surface, and
   said second body member including means for supporting said septum and being annular and having a cylindrical inner side surface,
   wherein said outer side surface of said first body member is adapted to interfit with said inner side surface of said second body member.

5. An access port according to claim 1, wherein said housing includes a second internal open face chamber extending along a second reference axis and defined by a second sidewall forming a second lateral boundary and being concave in the direction of said axis, and said access port further comprising:
   a second septum affixed to said housing and spanning the periphery of the open face of said second chamber, said second septum including a biocompatible, self-resealing, penetrable material; and
   a second cannula attached at a first end thereof to said housing and extending laterally therefrom, and having a second end thereof adapted to receive a catheter, said second cannula further having internal walls defining a second channel extending from said first end, along a channel axis from a point on said lateral boundary of, and in communication with, said second chamber, to said second end.

6. An access port according to claim 1, wherein the channel of said cannula has a radius R1 at said first end and a radius R2 at said second end, where R1 is greater than R2, and said catheter has a central passage with a radius R2.

7. An implantable vascular access system comprising:
   (a) a vascular access port including:
      a biocompatible housing having an internal open-faced chamber extending along a reference axis and defined by a concave sidewall forming a lateral boundary and being concave in the direction of said axis, and a bottom wall,
      a septum affixed to said housing and spanning the periphery of the open face of said chamber, said septum including a biocompatible, self-resealing, penetrable material,
      a cannula attached at a first end thereof to said housing and extending laterally therefrom, and having a second end thereof adapted to receive a catheter, said cannula further having internal walls defining a channel extending from said first end, along a channel axis from a point on said lateral boundary of, and in communication with, said chamber, to said second end, wherein the transition between said lateral boundary of said chamber and said internal walls of said canula is smooth;
   (b) a catheter having a central passage and an entry port defining a flow path to said central passage along a central axis; and
   (c) a coupling means for detachably coupling said cannula and said entry port, and for selectively establishing a continuous flow path between said chamber and said central passage with said channel axis and said central axis being coaxial.

8. A vascular access system according to claim 7, wherein said coupling means includes a resilient interface element disposed about and extending from said entry port, wherein the extending portion of said interface element is adapted to frictionally fit over the outer surface of said second end of said cannula,
   whereby said walls defining said channel at said second end and the inner surface of said central passage establish a substantially smooth bounded flow path.

9. A vascular access system according to claim 7, wherein said catheter has wirewound, reinforce sidewalls.

10. A vascular access system according to claim 7, wherein said end of said catheter opposite said entry port is beveled.

11. A vascular access system according to claim 10, wherein said end of said catheter opposite said entry port includes at least one lateral aperture adjacent thereto.

12. A vascular access system according to claim 7, wherein said end of said catheter opposite said entry port includes at least one lateral aperture adjacent thereto.

13. A vascular access system according to claim 7 further comprising a non-coring needle adapted to selectively penetrate said septum.

14. A vascular access system according to claim 13, wherein said needle includes a trocar point and includes at least one lateral aperture near said point.

15. A vascular access system according to claim 13, wherein said needle includes a solid point and includes at least one lateral aperture near said point.

16. A vascular access system according to claim 7 wherein said housing includes a second internal open face chamber extending along a second reference axis and defined by a second sidewall forming a second lateral boundary and being concave in the direction of said axis, and said access port further comprising:

a second septum affixed to said housing and spanning the periphery of the open face of said second chamber, said second septum including a biocompatible, self-resealing, penetrable material; and a second cannula attached at a first end thereof to said housing and extending laterally therefrom, and having a second end thereof adapted to receive a catheter, said second cannula further having internal walls defining a second channel extending from said first end, along a channel axis from a point on said lateral boundary of, and in communication with, said second chamber, to said second end.

17. A vascular access system according to claim 7, wherein the channel of said cannula has a radius R1 at said first end and a radius R2 at said second end, where R1 is greater than R2, and said catheter has a central passage having a radius R2.

* * * * *